(12) United States Patent
Nagano et al.

(10) Patent No.: US 6,767,901 B1
(45) Date of Patent: Jul. 27, 2004

(54) CICLESONIDE CONTAINED PHARMACEUTICAL COMPOSITION FOR APPLICATION TO MUCOSA

(75) Inventors: Atsuhiro Nagano, Tokyo (JP); Yoshihisa Nishibe, Yamaguchi (JP); Kazuya Takanashi, Tokyo (JP)

(73) Assignee: Altana Pharma AG, Constance (DE)

( * ) Notice: Subject to any disclaimer, the term of this patent is extended or adjusted under 35 U.S.C. 154(b) by 1 day.

(21) Appl. No.: 10/110,629

(22) PCT Filed: Oct. 20, 2000

(86) PCT No.: PCT/JP00/07350

§ 371 (c)(1),
(2), (4) Date: Jul. 15, 2002

(87) PCT Pub. No.: WO01/28562

PCT Pub. Date: Apr. 26, 2001

(30) Foreign Application Priority Data

Oct. 20, 1999 (JP) ............................................. 11-298185

(51) Int. Cl.⁷ ............................. A61K 9/08; A61K 9/12; A61K 9/72; A61K 31/58
(52) U.S. Cl. ........................ 514/174; 514/172; 514/826; 514/849; 514/853; 514/886; 514/946; 514/958; 514/975; 424/45; 424/46
(58) Field of Search ............................... 514/172, 174, 514/826, 849, 853, 886, 946, 958, 975; 424/45, 46

(56) References Cited

U.S. PATENT DOCUMENTS

2003/0008019 A1   1/2003   Nishibe et al.

FOREIGN PATENT DOCUMENTS

| WO | WO 92/14473 | 9/1992 |
| WO | WO 97/01337 | 1/1997 |
| WO | WO 98/52542 | 11/1998 |
| WO |    98/52542 | * 11/1998 |
| WO | WO 99/25359 | 5/1999 |
| WO | WO 99/37286 | 7/1999 |
| WO | WO 99/47144 | 9/1999 |

OTHER PUBLICATIONS

Machida, Minoru, et al., "Absorption of Recombinant Human Granulocyte Colony–Stimulating Factor (rhG–CSF) from Rat Nasal Mucosa". Pharmaceutical Research, vol. 10, No. 9, 1993, pp. 1372–1377.

Japanese unexamined Patent Publication 63–303931, Dec. 12, 1998 Abstract.

Japanese unexamined Patent Publication 60–123426, Jul. 2, 1985, Abstract.

Machida, M., et al. "Absorption of Recombinant Human Granulocyte Colony–Stimulating Factor (rhG–CSF) from Rat Nasal Mucosa", *Pharmaceutical Research*, vol. 10, No. 9, 1993.

* cited by examiner

*Primary Examiner*—John Pak
(74) *Attorney, Agent, or Firm*—Nath & Associates PLLC; Todd L. Juneau; Sheldon M. McGee

(57) ABSTRACT

The present invention provides a pharmaceutical composition for application to the mucosa to be used in drug therapy comprising a water-insoluble and/or water-low soluble substance, ciclesonide, and an aqueous medium, and having an osmotic pressure of less than 290 mOsm. This composition is superior over conventional pharmaceutical compositions for application to the mucosa, due to efficient and high ciclesonide retentivity and permeability to the submucosa or the blood at the mucosa.

22 Claims, No Drawings

US 6,767,901 B1

CICLESONIDE CONTAINED PHARMACEUTICAL COMPOSITION FOR APPLICATION TO MUCOSA

This application is a 371 of PCT/JP00/07350, filed on Oct. 20, 2000.

TECHNICAL FIELD

The present invention relates to a pharmaceutical composition for application to the mucosa to be used in drug therapy comprising a water-insoluble and/or water-low soluble substance, ciclesonide, and an aqueous medium, and having an osmotic pressure of less than 290 mOsm. More specifically, the present invention relates to a pharmaceutical composition for application to the mucosa comprising a water-insoluble and/or water-low soluble substance, ciclesonide, and an aqueous medium, and having an osmotic pressure of less than 290 mOsm, that is superior to conventional pharmaceutical compositions for application to the mucosa, due to ciclesonide retentivity and high ciclesonide permeability to the submucosa and the blood at the mucosa.

BACKGROUND ART

Application to the mucosa as a method of drug therapy has been recognized as a useful means of medication for such reasons as (1) it permits direct application to the affected area for diseases of local areas such as nasal mucosa, oral mucosa, and vaginal mucosa, (2) its immediate effects for systemic diseases can be expected as in the case of a nasal spray to the nasal mucosa and a suppository to the rectal mucosa, and (3) its application is easy compared to injection, as represented by an oral drug targeted at the intestinal mucosa, and the like. For example, pharmaceutical preparations for application to the mucosa have already been commercially available due to reason (1) in the case of nasal sprays for treatment of allergic rhinitis, and due to reason (2) in the case of suppositories to alleviate pain.

As pharmaceutical preparations for local mucus diseases, Saunders et al., (WO 92-14473), for example, provides a suspension preparation containing Tipredane as the main drug as the pharmaceutical preparation for treatment of allergic rhinitis. Also, Helzner et al., (WO 97-01337) provides a pharmaceutical preparation comprising an antihistaminic drug, a steroid and water as the pharmaceutical preparation for treatment of allergic rhinitis.

As the pharmaceutical preparations for systemic diseases, several methods have been provided that enhance the absorption of drugs through the mucosa. Nagata et al. (Japanese Unexamined Patent Publication (Kokai) No. 63 (1988)-303931), for example, provides a method of applying to the nasal cavity a growth hormone-releasing factor at the liquid form having an osmotic pressure ratio of 1 (an osmotic pressure of 290 mOsm) or lower as a method for enabling quick and efficient absorption of the a growth hormone-releasing factor through the nasal mucosa to the blood circulation. Furthermore, Ohwaki et al. (Japanese Unexamined Patent Publication (Kokai) No. 60 (1985)-123426) provides a method of applying to the nasal cavity a solution of secretin having an osmotic pressure ratio of 1 to 5 (an osmotic pressure of 290–1450 mOsm) and a pH of 2 to 5 as a method for enabling quick absorption of secretin through the nasal mucosa to blood circulation. Furthermore, Awatsu et al. (Pharm. Res. Vol. 10, No. 9, 1372-1377, 1993) provides a method of applying to the nasal mucosa a pharmaceutical solution to which polyoxyethylene 9-laurylether was added as an absorption enhancer as a method for enabling efficient absorption of a granulocyte colony-stimulating factor through the nasal mucosa to blood circulation.

Ciclesonide is a newly generated lipophilic corticoid. Due to its bioactivity, a commercially available ciclesonide contained pharmaceutical preparation for topical or systemic diseases is expected.

However, when a ciclesonide contained pharmaceutical preparation same composition as the conventional one is given to the mucosa, liquid-dripping can occur, or the pharmaceutical preparations are quickly excreted to the outside of the mucus tissue due to a mucociliary clearance function etc. before being adequately transported or permeated to the mucosa tissue. The method of using an absorption enhancer is yet to be realized because the absorption enhancer has the problem of irritating the nasal mucosa.

Thus, it is strongly desired to develop a ciclesonide contained pharmaceutical preparation for application to the mucosa, that allows the transport of an adequate amount of ciclesonide through the mucosa to the submucosa or the blood after the application to the mucosa.

DISCLOSURE OF THE INVENTION

The object of the present invention is to provide a pharmaceutical composition for application to the mucosa, that has efficient and high ciclesonide permeability through the mucosa to the submucosa or the blood when applied to the mucosa.

After intensive studies to attain the above first object, the present inventors have found that it is possible to provide a ciclesonide contained pharmaceutical preparation for application to the mucosa that is superior over conventional liquid composition due to efficient and high permeability through the mucosa to the submucosa or the blood, by formulating ciclesonide that contains a water-insoluble and/or water-low soluble substance and that has an osmotic pressure of less than 290 mOsm, and thereby have reached the present invention.

An enhanced absorption of a drug through the mucosa by controlling the osmotic pressure of a pharmaceutical preparation is disclosed in a patent to Osada or Ohwaki and has been reported in a paper by Awazu et al. (Pharm. Res. Vol. 10, No. 9, 1372-1377, 1993). However, these phenomena are only observed in aqueous solution preparations that do not contain a water-insoluble and/or water-low soluble substance, and thereby are essentially different from the ciclesonide contained pharmaceutical preparation of the present invention in which the inclusion of a water-insoluble and/or water-low soluble substance is essential. Furthermore, it has been shown in Osada's patent that absorption through the rat nasal mucosa of growth hormone releasing factor is higher when the preparation has an osmotic pressure ratio of 1 (osmotic pressure of 290 mOsm) or lower, and in Ohwaki's patent it is higher when secretin has an osmotic pressure ratio of 1 (osmotic pressure of 290 mOsm) or greater, and in Awazu's patent the absorption of granulocyte colony-stimulating factor is higher when the preparation has an osmotic pressure of 285 mOsm than 174 mOsm. So one cannot expect the fact that the ciclesonide absorption enhanced with decreasing an osmotic pressure.

The patent application by Saunders (WO 92-14473) and Helzner (WO 97-01337) described above describe pharmaceutical preparations containing a water-insoluble and/or water-low soluble substance. However, Saunders' patent application (WO 92-11473) makes no description of osmotic pressure of pharmaceutical preparations in general, in its claim, and merely describes in the specification that isotonicity is preferred, and Helzner's patent application makes no description of osmotic pressure of pharmaceutical preparations in general, and merely describes in the specification that the addition of an isotonic agent is preferred. From these patents, therefore, one cannot expect a drastic enhancement in the ciclesonide absorption at low osmotic pressures.

It is surprising therefore that the effect of enhancing the ciclesonide absorption at lower osmotic pressure through the mucosa is drastic when a water-insoluble or water-low soluble substance is coexistent.

Thus, the present invention provides an aqueous pharmaceutical composition for application to the mucosa comprising one or more water-insoluble substance and/or water-low soluble substance and ciclesonide, and having an osmotic pressure of less than 290 mOsm. The composition is a pharmaceutical composition for application to the mucosa that is superior over conventional pharmaceutical compositions for application to the mucosa, due to markedly efficient and high ciclesonide permeability to the submucosa or the blood at the mucosa.

EMBODIMENTS FOR CARRYING OUT THE INVENTION

In the present invention, the water-insoluble or water-low soluble substance may be any substance, and preferred examples include celluloses and more preferably crystalline celluloses.

The concentration of the water-insoluble and/or water-low soluble substance, that is present as solid particles in an aqueous medium in the first aspect of the present invention, is preferably 0.3% w/w or greater relative to the total amount of the preparation, and more preferably 1% to 10% w/w.

In any of the aspects of the present invention, preferably the water-insoluble or water-low soluble substance that is present as solid particles in an aqueous medium is homogeneously dispersed in the aqueous medium.

In any of the aspects of the present invention, preferably a water-soluble polymer is further added to the composition. Specifically, alginic acid, propylene glycol, pectin, low methoxyl pectin, guar gum, gum arabic, carrageenan, methyl cellulose, carboxymethyl cellulose sodium, xanthan gum, hydroxypropyl cellulose, hydroxypropyl methyl cellulose, and the like can be mentioned, and preferably carboxymethyl cellulose sodium, xanthan gum, and hydroxypropyl cellulose can be mentioned. In addition, as preferred combinations of a water-soluble polymers and water-insoluble and/or water-low soluble substance, there can be mentioned crystalline cellulose carmellose sodium that is a mixture of carboxymethyl cellulose sodium and crystalline cellulose. Preferably the concentration of these water-soluble polymers, when added, is 1% w/w to 30% w/w relative to the water-insoluble and/or water-low soluble substance.

It is an essential requirement in the first aspect of the present invention that the osmotic pressure of the pharmaceutical preparation is less than 290 mOsm, and preferably it is 150 mOsm or lower, more preferably 60 mOsm or lower, more preferably 30 mOsm or lower, and most preferably 10 mOsm or lower.

In the present invention, the addition of a substance for controlling osmotic pressure (osmotic pressure-controlling agent) is not particularly required, but when it is added any substance can be used. Specific examples include salts such as sodium chloride, and water-soluble sugars such as glucose, and among them salts such as sodium chloride are preferred.

In the present invention, a known surfactant can be added and specific examples include polysorbate 80, glycerin monostearate, polyoxyl stearate, Lauromacrogol, sorbitan oleate, sucrose fatty acid esters.

The amount of ciclesonide for use in the present invention is a therapeutically effective amount and can be determined depending on the type and the degree of the disease, the age and the weight of the patient, and the like. It is usually from the same to 20 times as much as the amount of each drug commonly used for injection, more preferably from the same to 10 times as much.

The concentration of ciclesonide of the present invention is preferably 0.01% w/w to 1% w/w relative to the total amount of the pharmaceutical preparation, and most preferably 0.05% w/w to 0.5% w/w.

In order to improve the physical properties, appearances, or smells of the composition of the present invention, a known antiseptic, a pH controlling agent, a preservative, a buffer, a colorant, a smell corrigent, and the like may be added, as desired. For example, benzalkonium chloride as the antiseptic, hydrochloric acid as the pH controlling agent, ascorbic acid as the preservative, citric acid and salts thereof as the buffer, Red No. 2 as the colorant, menthol as the smell corrigent may be mentioned.

The mucosa to which the present invention is applied may be any mucosa. Specific examples include intestinal mucosa, gastric mucosa, nasal mucosa, tracheal/bronchial/pulmonary mucosa, mucosa of oral cavity, rectal mucosa, vaginal mucosa, and the like, and nasal mucosa is most preferred.

The composition of the present invention may be formulated in a dosage form suitable for administration as a pharmaceutical preparation. It may contain an indirect dosage form such as an oral formulation for administration to the gastric and intestinal mucosa. In this case, the composition of the present invention may be filled in a gastric or enteric capsule, for example, and the composition is exposed at the desired site of mucosa. As another dosage form, when given to the rectal mucosa, the present invention may be filled in a capsule in a unit dosage form, which is administered as a suppository. When given to the oral mucosa, nasal mucosa, or vaginal mucosa, the composition of the present invention may be filled in a spray-type container, a fixed amount of which is sprayed to the oral cavity, nose, or vagina. When given to the tracheal/bronchial/pulmonary mucosa, the present invention may be filled to an inhalation-type container, which is allowed to be inhaled into the trachea, bronchus, or lung.

EXAMPLES

The present invention will now be explained with reference to the following examples.

Ciclesonide was obtained from Byk Gulden Lomberg Chemische Fabrik GmbH, crystalline cellulose carmellose sodium, Avicel™ RC-591NF, was manufactured by Asahi Chemical Industry, Co., Ltd., benzalkonium chloride was from Nakalai Tesque, glucose was from Wako Pure Chemicals.

Example 1

A ciclesonide contained composition No. 1 for application to the mucosa comprising the components described in the following Table 1 was prepared. For this pharmaceutical preparation, osmotic pressure was measured using the Micro-Osmometer Model 3MO from Advance Instruments, Inc. The result is shown in Table 1.

One hundred μl of the composition No. 1 for application to the nasal mucosa was sprayed to the unilateral nasal cavity of rabbits (Japanese White, male, weighing 3 kg) using a commercially available suspension device. At 5, 15 and 30 minutes after the administration, the mucus flown from the nasal cavity to the esophaguswere collected and the ciclesonide concentrations of them were determined by HPLC.

Then, 30 minutes after the administration, residual ciclesonide in the nasal cavity were washed with ethanol and the ciclesonide concentrations of washing fluid were determined by HPLC.

The clearance amount of ciclesonide from the nasal cavity to the esophagus was calculated by the flown mucus amount and their ciclesonide concentrations. Then the residual ciclesonide amount was calculated by administered ciclesonide amount and collected ciclesonide amount. The mean values of five rabbits are shown in Table 1.

TABLE 1

| No. | Composition | Osmotic pressure (mOsm) | Clearance amount (%) 5 min | 15 min | 30 min | Residual amount (%) |
|---|---|---|---|---|---|---|
| 1 | Ciclesonide: 0.2% w/w Crystalline cellulose carmellose sodium: 1.7% w/w Benzalkonium chloride: 0.02% w/w | 5 | 6.75 | 12.97 | 20.41 | 39.81 |

Comparative Example 1

A ciclesonide contained composition No. 2 for application to the mucosa comprising the components described in the following Table 2 was prepared. For this pharmaceutical preparation, osmotic pressure was measured using the Micro-Osmometer Model 3MO from Advance Instruments, Inc. The result is shown in Table 2.

One hundred μl of the composition No. 2 for application to the nasal mucosa was sprayed to the unilateral nasal cavity of rabbits (Japanese White, male, weighing 3 kg) using a commercially available suspension device. At 5, 15 and 30 minutes after the administration, the mucus flown from the nasal cavity to the esophagus were collected and the ciclesonide concentrations of them were determined by HPLC.

Then, 30 minutes after the administration, residual ciclesonide in the nasal cavity were washed with ethanol and the ciclesonide concentrations of washing fluid were determined by HPLC.

The clearance amount of ciclesonide from the nasal cavity to the esophagus was calculated by the flown mucus amount and their ciclesonide concentrations. Then the residual ciclesonide amount was calculated by administered ciclesonide amount and collected ciclesonide amount. The mean values of five rabbits are shown in Table 2.

TABLE 2

| No. | Composition | Osmotic pressure (mOsm) | Clearance amount (%) 5 min | 15 min | 30 min | Residual amount (%) |
|---|---|---|---|---|---|---|
| 2 | Ciclesonide: 0.2% w/w Crystalline cellulose carmellose sodium: 1.7% w/w Benzalkonium chloride: 0.02% w/w Glucose: 5.7% w/w | 330 | 39.85 | 51.11 | 55.08 | 17.76 |

The clearance amount of ciclesonide contained composition for application to the mucosa dramatically increased with higher osmotic pressure. At thirty minutes after administration of Composition No. 2 (330 mOsm) the clearance amount of ciclesonide was 2.5-fold as much as that of Composition No. 1 (5 mOsm) and Composition No. 1 (5 mOsm) the residual ciclesonide amount was 2-fold as much as that of Composition No. 2 (330 mOsm). These results show that the ciclesonide retentivity was enhanced by lowering the osmotic pressure from 330 mOsm to 5 mOsm.

Enhanced ciclesonide retentivity leaves a large amount of residual ciclesonide on the mucus, and it makes gradient of ciclesonide concentration around the mucosa. Thus the ciclesonide permeability to the submucosa and the blood at the mucosa is enhanced and this state is retained.

INDUSTRIAL APPLICABILITY

Thus, the present invention provides a pharmaceutical composition for application to the mucosa, that has efficient and high ciclesonide permeability through the mucosa to the submucosa or the blood when applied to the mucosa.

By using such a composition of the present invention for application to the mucosa, effects equal to or greater than those obtained with the same composition as the conventional compositions can be obtained even at smaller doses or lower administration frequencies than the conventional methods. This can lead to reduction in side effects.

Thus, the present invention is extremely useful in terms of therapeutic and economic effects for ciclesonide therapies that employ application to the mucosa.

What is claimed is:

1. An aqueous pharmaceutical composition for application to the mucosa, comprising one or more water-insoluble and/or water-low soluble substance, and ciclesonide, and having an osmotic pressure of 150 mOsm or less.

2. The pharmaceutical composition for application to the mucosa according to claim 1, wherein said osmotic pressure is 60 mOsm or less.

3. The pharmaceutical composition for application to the mucosa according to claim 1, wherein said osmotic pressure is 30 mOsm or less.

4. The pharmaceutical composition for application to the mucosa according to claim 1, wherein said osmotic pressure is 10 mOsm or less.

5. The pharmaceutical composition for application to the mucosa according to claim 1, further comprising an osmotic pressure-controlling agent.

6. The pharmaceutical composition for application to the mucosa according to claim 5, wherein said osmotic pressure-controlling agent is a salt.

7. The pharmaceutical composition for application to the mucosa according to claim 6, wherein said osmotic pressure-controlling agent is sodium chloride.

8. The pharmaceutical composition for application to the mucosa according to claim 5, wherein said osmotic pressure-controlling agent is a water-soluble sugar.

9. The pharmaceutical composition for application to the mucosa according to claim 8, wherein said osmotic pressure-controlling agent is glucose.

10. The pharmaceutical composition for application to the mucosa according to claim 1, wherein said water-insoluble and/or water-low soluble substance is a cellulose.

11. The pharmaceutical composition for application to the mucosa according to claim 10, wherein said cellulose is crystalline cellulose.

12. The pharmaceutical composition for application to the mucosa according to claim 1, wherein said one or more water-insoluble and/or water-low soluble substance is present as solid particles in an aqueous medium.

13. The pharmaceutical composition for application to the mucosa according to claim 1, wherein said one or more water-insoluble and/or water-low soluble substance is dispersed as solid particles in an aqueous medium.

14. The pharmaceutical composition for application to the mucosa according to claim 1, further comprising a water-soluble polymer substance.

15. The pharmaceutical composition for application to the mucosa according to claim 14, wherein said water-soluble polymer is one or more selected from the group consisting of alginic acid, propylene glycol, pectin, low methoxyl pectin guar gum, gum arabic, carrageenan, methyl cellulose, carboxymethyl cellulose sodium, xanthan gum, hydroxypropyl cellulose, and hydroxypropyl methyl cellulose.

16. The pharmaceutical composition for application to the mucosa according to claim 14, wherein said water-soluble polymer is carboxymethyl cellulose sodium.

17. The pharmaceutical composition for application to the mucosa according to claim 14, wherein said water-soluble polymer is xanthan gum.

18. The pharmaceutical composition for application to the mucosa according to claim 15, wherein said water-soluble polymer is hydroxypropyl methyl cellulose.

19. The pharmaceutical composition for application to the mucosa according to claim 14, wherein the combination of said water-insoluble substance and water-soluble polymer is crystalline cellulose carmellose sodium.

20. The pharmaceutical composition for application to the mucosa according to claim 1, further comprising a surfactant.

21. The pharmaceutical composition for application to the mucosa according to claim 20, wherein said surfactant is polysorbate 80.

22. The pharmaceutical composition ion to the mucosa according to claim 1, mucosa is nasal mucosa.

* * * * *

UNITED STATES PATENT AND TRADEMARK OFFICE
CERTIFICATE OF CORRECTION

PATENT NO. : 6,767,901 B1
DATED : July 27, 2004
INVENTOR(S) : Nagano et al.

It is certified that error appears in the above-identified patent and that said Letters Patent is hereby corrected as shown below:

Column 8,
Line 24, should read -- The pharmaceutical composition for application to the mucosa according to claim 1, wherein said mucosa is nasal mucosa. --

Signed and Sealed this

Fourteenth Day of December, 2004

JON W. DUDAS
*Director of the United States Patent and Trademark Office*